United States Patent
Evangelou et al.

(10) Patent No.: US 11,227,690 B1
(45) Date of Patent: Jan. 18, 2022

(54) MACHINE LEARNING PREDICTION OF THERAPY RESPONSE

(71) Applicant: OPENDNA LTD., Haifa (IL)

(72) Inventors: Evangelos Evangelou, Haifa (IL); Eran Feldhay, Haifa (IL); Erez Ornan, Haifa (IL)

(73) Assignee: OPENDNA LTD., Haifa (IL)

( * ) Notice: Subject to any disclaimer, the term of this patent is extended or adjusted under 35 U.S.C. 154(b) by 0 days.

(21) Appl. No.: 17/020,002

(22) Filed: Sep. 14, 2020

(51) Int. Cl.
| | |
|---|---|
| *G16H 50/20* | (2018.01) |
| *G16H 50/30* | (2018.01) |
| *G16H 50/70* | (2018.01) |
| *G16B 40/00* | (2019.01) |
| *G16H 70/40* | (2018.01) |
| *G06N 20/00* | (2019.01) |
| *G16B 20/20* | (2019.01) |
| *G16H 70/20* | (2018.01) |
| *G16H 10/20* | (2018.01) |

(52) U.S. Cl.
CPC ............ *G16H 50/20* (2018.01); *G06N 20/00* (2019.01); *G16B 20/20* (2019.02); *G16B 40/00* (2019.02); *G16H 10/20* (2018.01); *G16H 50/30* (2018.01); *G16H 50/70* (2018.01); *G16H 70/20* (2018.01); *G16H 70/40* (2018.01)

(58) Field of Classification Search
CPC .. G16H 50/20–30; G16H 50/30; G16H 50/70; G16H 70/40; G16H 10/20; G16H 70/20; G06N 20/00; G16B 20/20; G16B 40/00
See application file for complete search history.

(56) References Cited

U.S. PATENT DOCUMENTS

| | | | |
|---|---|---|---|
| 9,384,323 B1* | 7/2016 | Fernandez | ............. G16H 10/20 |
| 2003/0143608 A1 | 7/2003 | Filigheddu et al. | |
| 2005/0181386 A1 | 8/2005 | Diamond et al. | |
| | (Continued) | | |

FOREIGN PATENT DOCUMENTS

JP          4394384 B2      1/2010

OTHER PUBLICATIONS

Dipender Gill et al, "Use of Genetic Variants Related to Antihypertensive Drugs to Inform on Efficacy and Side Effects", Circulation, 2019, Issue 140, pp. 270-279.

(Continued)

*Primary Examiner* — Michael Tomaszewski
*Assistant Examiner* — Jay M. Patel
(74) *Attorney, Agent, or Firm* — The Roy Gross Law Firm, LLC; Roy Gross (57) ABSTRACT

A method comprising: receiving, for each of a plurality of subjects, each having a specified type of cardiovascular or cardiometabolic disease and receiving at least one specified therapy from a set of therapies for treating cardiovascular and cardiometabolic diseases, a first score representing a first genetic predisposition in said subject to respond to one or more of said set of therapies; at a training stage, training a machine learning model on a training set comprising: (i) all of said first scores, and labels associated with a response in each of said subjects to said at least one specified therapy; and at an inference stage, apply said trained machine learning model to a target said first score received with respect to a target subject, to predict a response in said target subject to at least one of said therapies in said set.

19 Claims, 2 Drawing Sheets

(56) References Cited

U.S. PATENT DOCUMENTS

| | | | |
|---|---|---|---|
| 2010/0063930 A1* | 3/2010 | Kenedy | G16H 10/60 |
| | | | 705/51 |
| 2010/0167947 A1 | 7/2010 | Sadee et al. | |
| 2017/0175193 A1 | 6/2017 | Snyder et al. | |
| 2017/0292159 A1* | 10/2017 | Shiffman | A61P 9/10 |
| 2019/0345557 A1* | 11/2019 | Khera | C12Q 1/6883 |
| 2020/0321123 A1* | 10/2020 | Neumann | G16H 50/20 |
| 2020/0342958 A1* | 10/2020 | McGovern | C12Q 1/6883 |

OTHER PUBLICATIONS

Evangelos Evangelou et al, "Genetic analysis of over one million people identifies 535 new loci associated with blood pressure traits", Nature Genetics, Oct. 2018, Issue 50 vol. 10, pp. 1412-1425.

Bjarni J Vilhjálmsson et al, "Modeling Linkage Disequilibrium Increases Accuracy of Polygenic Risk Scores", American Journal of Human Genetics, Oct. 1, 2015, Issue 97, vol. 4, pp. 576-592.

Daniel Gianola et al, "Predicting genetic predisposition in humans: The promise of whole-genome markers", Nature Reviews Genetics, Nov. 2010, Issue 11 vol. 12, pp. 880-886.

* cited by examiner

MACHINE LEARNING PREDICTION OF THERAPY RESPONSE

FIELD OF THE INVENTION

The present invention relates to the field of machine learning.

BACKGROUND OF THE INVENTION

Hypertension (HTN) is the strongest modifiable risk factor for cardiovascular disease, and is the most common condition seen in the primary care setting. Globally, HTN is the leading cause of death and disability-adjusted life-years worldwide. In the United States, HTN affects ~80 million individuals with over 5 million new diagnoses each year.

Effective treatment for rapid reductions in blood pressure (BP) is important for survival in HTN subjects, as end organ damage can occur quickly. Unfortunately, BP control rates are very poor with only half of HTN subjects receiving treatment achieving control.

Each common class of BP medication (diuretic, angiotensin-converting enzyme (ACE) inhibitors (ACEIs), angiotensin-II receptor blockers, beta-blockers) has an effectiveness rate of approximately 50%, suggesting a significant genetic component to therapy efficacy.

Hypertension is a highly multifactorial disease modulated by multiple susceptibility genes, suggesting a strong genetic determinant to the BP response to therapies. Genome-wide association studies and candidate gene studies have identified blood pressure-associated genes that may be targeted by antihypertensive medication, indicating that the effectiveness may be improved using genetics. However, there is a general lack of genetically-informed therapy decisions in clinical practice today.

The foregoing examples of the related art and limitations related therewith are intended to be illustrative and not exclusive. Other limitations of the related art will become apparent to those of skill in the art upon a reading of the specification and a study of the figures.

SUMMARY OF INVENTION

The following embodiments and aspects thereof are described and illustrated in conjunction with systems, tools and methods which are meant to be exemplary and illustrative, not limiting in scope.

There is provided, in an embodiment, a system comprising: at least one hardware processor; and a non-transitory computer-readable storage medium having stored thereon program code, the program code executable by the at least one hardware processor to: receive, for each of a plurality of subjects, each having a specified type of cardiovascular or cardiometabolic disease and receiving at least one specified therapy from a set of therapies for treating cardiovascular and cardiometabolic diseases, a first score representing a first genetic predisposition in the subject to respond to one or more of the set of therapies, at a training stage, train a machine learning model on a training set comprising: (i) all of the first scores, and (ii) labels associated with a response in each of the subjects to the at least one specified therapy, and at an inference stage, apply the trained machine learning model to a target the first score received with respect to a target subject, to predict a response in the target subject to at least one of the therapies in the set.

There is also provided, in an embodiment, a method comprising receiving, for each of a plurality of subjects, each having a specified type of cardiovascular or cardiometabolic disease and receiving at least one specified therapy from a set of therapies for treating cardiovascular and cardiometabolic diseases, a first score representing a first genetic predisposition in the subject to respond to one or more of the set of therapies; at a training stage, training a machine learning model on a training set comprising: (i) all of the first scores, and (ii) labels associated with a response in each of the subjects to the at least one specified therapy; and at an inference stage, apply the trained machine learning model to a target the first score received with respect to a target subject, to predict a response in the target subject to at least one of the therapies in the set.

There is further provided, in an embodiment, a computer program product comprising a non-transitory computer-readable storage medium having program code embodied therewith, the program code executable by at least one hardware processor to receive, for each of a plurality of subjects, each having a specified type of cardiovascular or cardiometabolic disease and receiving at least one specified therapy from a set of therapies for treating cardiovascular and cardiometabolic diseases, a first score representing a first genetic predisposition in the subject to respond to one or more of the set of therapies; at a training stage, train a machine learning model on a training set comprising: (i) all of the first scores, and (ii) labels associated with a response in each of the subjects to the at least one specified therapy; and at an inference stage, apply the trained machine learning model to a target the first score received with respect to a target subject, to predict a response in the target subject.

In some embodiments, with respect to each of the plurality of subjects, the first score is a polygenic score calculated, based, at least in part, on identifying in the subject single nucleotide polymorphisms (SNP) associated with a predisposition to respond to one of the therapies in the set.

In some embodiments, the receiving further comprises receiving a second score representing a second genetic predisposition in the subject with respect to the disease or a trait associated with the disease, and wherein the training set further comprises all of the second scores.

In some embodiments, with respect to each of the plurality of subjects, the second score is a polygenic score calculated, based, at least in part, on identifying in the subject SNPs associated with blood pressure risk.

In some embodiments, the first and second scores are calculated in real time based, at least on part, on parallel calculation per each chromosome.

In some embodiments, at least some of the SNPs are selected when they are located in the in promoter or enhancer areas of genes.

In some embodiments, the set of therapies is selected from the group consisting of: Ace inhibitors; Angiotensin receptor lockers; Thiazides; Thiazide like; Beta blockers; Alpha antagonists; Alpha blockers; Vasodilators; Aldosterone antagonist; Renal denervation and Barostimulation Biguanides; Sulfonylureas; Meglitinide derivatives; Alpha-glucosidase inhibitors; Thiazolidinediones (TZDs); Glucagon-like peptide-1 (GLP-1) agonists; Dipeptidyl peptidase IV (DPP-4) inhibitors; Selective sodium-glucose transporter-2 (SGLT-2) inhibitors; Insulins; Amylinomimetics; Bile acid sequestrants; Dopamine agonists and bariatric surgery for Type 2 Diabetes; Antilipemic agents; Nicotinic acids; Bile sequestrants; Aspirin, Anti coagulants; Anti platelet; Nitrates; anti-inflammatory agents; DNA methyltransferase inhibitors; antiarrhythmic agents; cardiac and neurological interventions; heart transplants; Digoxin; Ionotropic agents;

ivabradine; sacubitril/valsartan; histone deacetylase inhibitors; and lifestyle regimens such as dietary regimens and physical activity regimens.

In some embodiments, the disease or a trait associated with the disease is one of: hypertension, systolic blood pressure (SBP), diastolic blood pressure (DBP), high blood glucose levels, diabetes, hypercholesterolemia, high lipids levels, coronary heart disease, heart failure, obesity, and arrhythmia.

In the response in each of the subjects and the target subject to the one or more specified therapies comprises at least one: lowering of SBP, lowering of DBP, lowering of blood glucose levels, lowering of blood lipids levels, improving of coronary heart disease symptoms, improving of heart failure symptoms, lowering weight, and improving of arrhythmia symptoms.

In some embodiments, the training set further comprises, with respect to at least some of the subjects, labels associated with clinical data selected from the group consisting of: SBP, DBP, age, sex, body mass index (BMI), diet parameters, cholesterol parameters, co-morbidities, physical activity parameters, family history of cardiovascular disease and/or cardiometabolic disease, stress parameters, alcohol consumption parameters, and smoking and tobacco usage, lab results, imaging studies, ECG studies additional medication, response and adverse effect of medications, and allergies.

In addition to the exemplary aspects and embodiments described above, further aspects and embodiments will become apparent by reference to the figures and by study of the following detailed description.

DETAILED DESCRIPTION OF THE INVENTION

Disclosed are a system, method, and computer program product which provide for a machine learning model configured to predict a response in a subject to prescribed therapy for a cardiovascular or cardiometabolic disease.

In some embodiments, the present disclosure provides for training a machine learning model using a training dataset comprising data regarding genetic predisposition in each of the cohort of subjects to develop cardiovascular or cardiometabolic disease and/or one or more traits associated with the cardiovascular or cardiometabolic disease. In some embodiments, each, or at least some, of the subjects in the cohort receive one or more treatments, e.g., one or more pharmacotherapies, for the specified cardiovascular or cardiometabolic disease.

In some embodiments, the genetic predisposition data may comprise a polygenic score (PS) associated with a genetic predisposition in a subject to develop, e.g., hypertension, including systolic blood pressure (SBP) and/or diastolic blood pressure (DBP); high blood glucose levels; diabetes; hypercholesterolemia; high lipids levels; coronary heart disease; heart failure; and/or arrhythmia. In some embodiments, the genetic predisposition data may additionally or alternatively comprise a polygenic score associated with a genetic predisposition in a subject to respond to one or more therapies associated with a cardiovascular or cardiometabolic disease.

Accordingly, in some embodiments, the present disclosure provides a computational approach for training a machine learning model to predict a response in subjects. The present disclosure will discuss extensively aspects of the present invention associated with predicting response subjects having a cardiovascular or cardiometabolic disease. The term "response" as used herein refers to a set of subject-driven factors that may limit or counteract the effectiveness of one or more treatment or therapy modalities applied to the subject. However, the present method may be equally effective in predicting treatment and/or therapy response in the context of other diseases or disorders.

In some embodiments, a trained machine learning model of the present disclosure may provide for predicting a response of a subject diagnosed with a specified cardiovascular or cardiometabolic disease to a specified treatment or therapy.

In some embodiments, a training dataset for a machine learning model of the present disclosure may comprise genetic data associated with a polygenic score representing predisposition and/or susceptibility in a subject to the cardiovascular or cardiometabolic disease and/or one or more traits associated with the cardiovascular or cardiometabolic disease. In some embodiments, a training dataset for a machine learning model of the present disclosure may comprise genetic data associated with a polygenic score representing predisposition and/or susceptibility in a subject to respond to one or more treatments or therapies associated with a cardiovascular or cardiometabolic disease.

In some embodiments, a trained machine learning model of the present disclosure provides for predicting a response of a subject to the specified treatment or therapy as a binary value, e.g., 'yes/no,' 'responsive/non-responsive,' or 'favorable/non-favorable response.' In some embodiments, the prediction may be expressed on a scale and/or be associated with a confidence parameter. Accordingly, in some embodiments, a machine learning model of the present disclosure may provide for predicting a response rate and/or success rate of a specified treatment in a subject, e.g., the likelihood of a favorable response of a subject to the specified treatment or therapy. For example, in some embodiments, the prediction may be expressed in discrete categories and/or on a scale comprising, e.g., 'complete response,' 'partial response,' 'stable disease,' 'progressive disease,' and 'hyperprogression disease.' In some embodiments, the prediction may indicate whether a response by a subject is associated with adverse or any other secondary effects, e.g., side-effects. In some embodiments, additional and/or other scales and/or thresholds and/or response criteria may be used, e.g., a gradual scale of 1 (non-responsive) to 5 (responsive).

In certain embodiments, the terms "treatment" or "therapy" refer to multiple sessions of treatment of a subject. In specific embodiments, the term "pre-treatment" refers to a time point before the first session of treatment, and the term "on treatment" refers to a time point during the course of treatment. In alternative specific embodiments, the term "on treatment" refers to a time point between one or more sessions of treatment.

In the present context, the terms "treatment" or "therapy" refer to any method of treatment of cardiovascular or cardiometabolic disease, including but not limited to, Ace inhibitors; Angiotensin receptor lockers; Thiazides; Thiazide like; Beta blockers; Alpha antagonists; Alpha blockers; Vasodilators; Aldosterone antagonist; Renal denervation and Barostimulation Biguanides; Sulfonylureas; Meglitinide derivatives; Alpha-glucosidase inhibitors; Thiazolidinediones (TZDs); Glucagonlike peptide-1 (GLP-1) agonists; Dipeptidyl peptidase IV (DPP-4) inhibitors; Selective sodium-glucose transporter-2 (SGLT-2) inhibitors; Insulins; Amylinomimetics; Bile acid sequestrants; Dopamine agonists and bariatric surgery for Type 2 Diabetes; Antilipemic agents; Nicotinic acids; Bile sequestrants; Aspirin, Anti coagulants; Anti platelet; Nitrates; anti-inflammatory agents; DNA methyltransferase inhibitors; antiarrhythmic agents; cardiac and neurological interventions; heart transplants; Digoxin; Ionotropic agents; ivabradine; sacubitril/valsartan; histone deacetylase inhibitors; and/or lifestyle regimens such as dietary regimens and/or physical activity regimens.

A potential advantage of the present disclosure is, therefore, in that it provides a tool for assisting clinicians in making treatment recommendations informed by genetic data associated with drug activity in cardiovascular or cardiometabolic disease. The present method does not require any dedicated hardware or device, and may be implemented using any widely used computing device, such as a desktop computer, laptop computer, tablet, smartphone, and the like.

Figure 1:
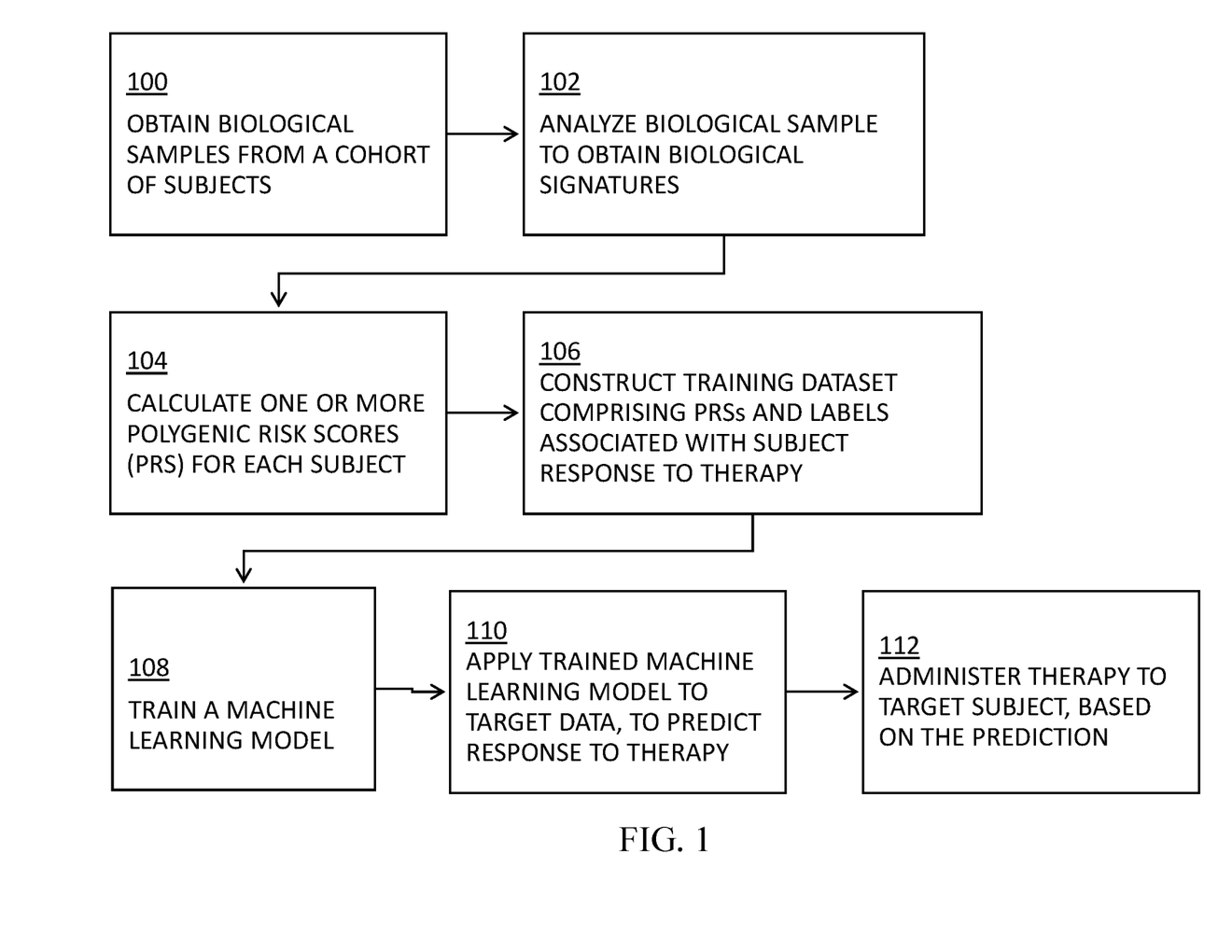
FIG. 1 is a flowchart of the functional steps in a method for a machine learning model configured to predict a response in a subject to prescribed therapy for a cardiovascular or cardiometabolic disease, according to some embodiments of the present disclosure.
Figure 2:
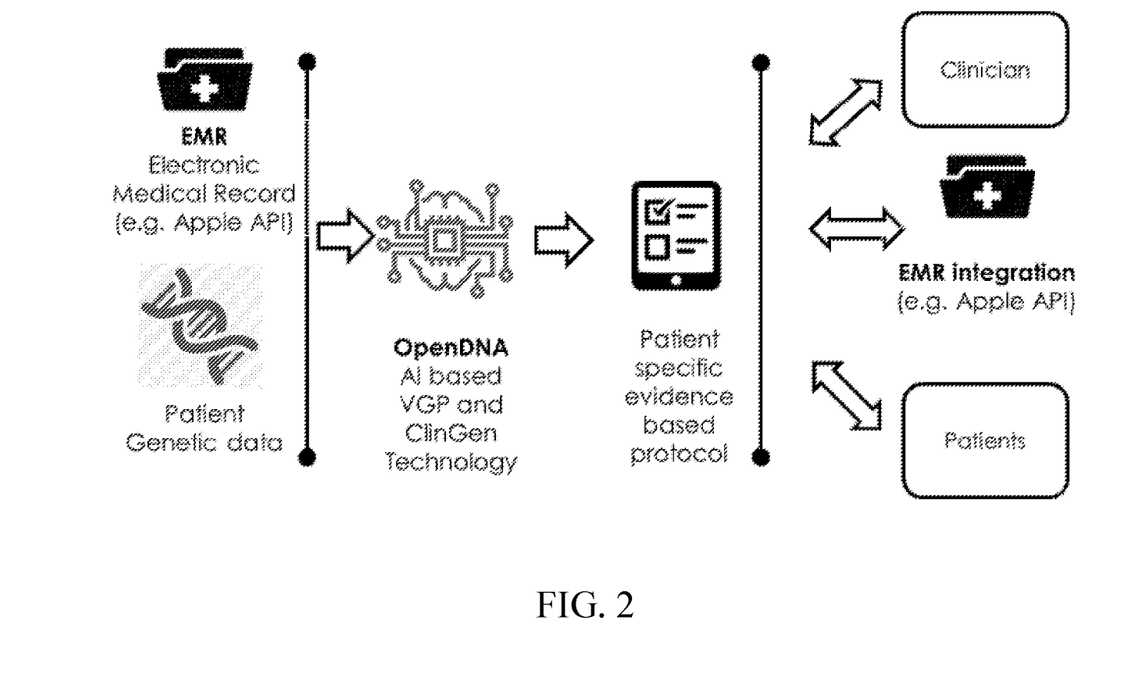
FIG. 2 is a schematic illustration of the process steps of FIG. 1, according to some embodiments of the present disclosure.

FIG. 1 is a flowchart of the functional steps in a method for training a machine learning model to predict a response in a subject to prescribed therapy for a cardiovascular or cardiometabolic disease, according to some embodiments of the present disclosure. FIG. 2 is a schematic illustration of the process steps of FIG. 1.

In some embodiments, at step 100, a plurality of biological samples may be acquired or received from a cohort of subjects, e.g., a predefined population of subjects having a specified type of disease. In some embodiments, a cohort or predefined population comprises subjects having a specified type of cardiovascular or cardiometabolic disease and receiving a specified type of treatment and/or therapy associated with the specified type of disease. In certain embodiments of the method according to the invention, the cohort or predefined population of subjects is based on, or determined according to, any one of: disease type, disease stage, disease therapy, treatment history, clinical profile, laboratory results, imaging studies, and any combination thereof. In some embodiments, a cohort assembled for the purposes of the present disclosure may comprise a plurality of subjects having the same and/or a similar and/or an associated disease and/or category of diseases and/or syndromes and/or conditions, and/or associated diseases, syndromes and/or conditions. In some embodiments, with respect to at least some of the subjects in the cohort, the specified disease and/or conditions may be at different stages and/or be combined with co-morbidities and/or diseases. In some embodiments, a specified disease of the present disclosure may be expressed in terms of broad categories (e.g., cardiovascular or cardiometabolic), sub-types (e.g., coronary artery diseases), and/or sub-categories (e.g., angina).

In some embodiments, the disease is cardiovascular disease. Types of cardiovascular diseases are well known in the art, and examples of classes of cardiovascular include, but are not limited to, any diseases that involve the heart or blood vessels, including coronary artery diseases (CAD) such as angina and myocardial infarction (commonly known as a heart attack); stroke; heart failure; hypertensive heart disease; rheumatic heart disease; cardiomyopathy; abnormal heart rhythms; congenital heart disease; valvular heart disease; carditis; aortic aneurysms; peripheral artery disease; thromboembolic disease; and venous thrombosis.

In some embodiments, the disease is cardiometabolic disease, including, but not limited to, e.g., diabetes or any other diseases that involve cardiometabolic syndrome (CMS) or any combination of metabolic dysfunctions characterized by insulin resistance, impaired glucose tolerance, dyslipidemia, hypertension, and central adiposity.

In some embodiments, the disease may be hypertension (HTN); low blood pressure; or renal disease.

In some embodiments, the disease is an autoimmune disease. In some embodiments, the disease is a genetic disease. In some embodiments, the disease is an infectious disease. In some embodiments, the disease is a bacterial, viral or fungal infection. In some embodiments, the disease is an inflammatory disease. In some embodiments, the disease is a respiratory disease. In some embodiments, the disease is degenerative disease. In some embodiments, the disease is a neurodegenerative disease. In some embodiments, the disease is a metabolic disease.

In some embodiments, biological samples may include any type of biological sample obtained from an individual, including body tissues, body fluids, body excretions, cells or other sources. Body fluids may be whole blood, blood plasma, blood serum, peripheral blood mononuclear cells, lymph, urine, saliva, semen, synovial fluid and spinal fluid, fresh or frozen. In certain embodiments of the method according to the invention, the biological sample(s) is blood plasma, whole blood, blood serum, cerebrospinal fluid (CSF), or peripheral blood mononuclear cells (PBMCs). In specific embodiments, the biological sample(s) is blood plasma. In alternative specific embodiments, the biological sample(s) is CSF. In some embodiments, the biological sample(s) is a peripheral blood mononuclear cell (PBMC) sample. In some embodiments, the biological sample(s) is a blood sample.

In some embodiments, a cohort of the present disclosure comprises a group of subjects with similar phenotype and receiving a similar treatment. However, the cohort definition may vary according to the classification per cohort and biological common denominator of the participating subjects. In some embodiments, a cohort of the present disclosure may comprise subjects of, e.g., different demographics (e.g., sex, age, ethnicity), clinical measurements, disease stage, disease history, disease treatment history, general medical history (e.g., including smoking history and drinking habits, background diseases) genetic information, physical parameters, laboratory results, imaging studies, and the like.

In some embodiments, subjects in the cohort may undergo and/or receive different types of treatments, e.g., mono therapy, combo therapy, multi-stage or multi-session therapy, and/or multi-modality therapy.

In some embodiments, the biological samples may be obtained from each subject in the cohort, or from at least some of the subjects, at specified times before, during, and/or after the conclusion of, a course of therapy. In some embodiments, the biological samples may be obtained from each subject, or from at least some of the subjects, at specified one or more stages and/or points and/or steps before, during, and/or after the conclusion of, a course of therapy, e.g., pre-therapy, on-therapy, and/or post-therapy.

In some embodiments, at step 102, each of, or at least some of, the biological samples may be analyzed to identify a plurality of biomarkers and/or to extract a biological signature. In some embodiments, the analysis obtains, e.g., a proteomic profile comprising protein expression for each of the samples. In some embodiments, the protein expressions so obtained may identify the proteins in each analyzed biological sample. In some embodiments, additional and/or other analyses may be performed with respect to the biological samples, to obtain, e.g., one or more of DNA profile; RNA profile; single cell RNA sequencing; metabolomics; microbiome; genomics; epigenomics; and MicroRNA.

In some embodiments, at step 104, one or more genetic scores, e.g., polygenic scores (PS) may be calculated with respect to at least some of the subjects, based, at least in part, on identifying in the subject single nucleotide polymorphisms (SNP) associated with a predisposition to developing the cardiovascular or cardiometabolic disease and/or one or more traits associated with the cardiovascular or cardiometabolic disease.

Polygenic scores (PS) computed from genome-wide association study (GWAS) summary statistics have proven valuable for predicting disease risk and understanding the genetic architecture of complex traits. PSs can also be used for drawing inferences about genetic architectures within and across traits.

In some embodiments, the PSs may be associated with a genetic predisposition in a subject to respond to one or more therapies associated with a cardiovascular or cardiometabolic disease. For example, PSs may be based on identified genetic proxies for the effect of antihypertensive drug classes.

In some embodiments, the PSs may additionally or alternatively comprise a polygenic score associated with a genetic predisposition in a subject to develop, e.g., one or more of hypertension, including systolic blood pressure (SBP) and/or diastolic blood pressure (DBP); high blood glucose levels; diabetes; hypercholesterolemia; high lipids levels; coronary heart disease; heart failure; stroke; peripheral artery disease; obesity; and/or arrhythmia.

The following disclosure will discuss extensively applications of the present method with respect to cardiovascular and cardiometabolic disease, wherein the associated trait is blood pressure, including systolic blood pressure (SBP), diastolic blood pressure (DBP) and pulse pressure (PP), and wherein therapy response is determined as a response to one or more therapies from a specified set of antihypertensive pharmacotherapies.

In some embodiments, generating PSs for a cohort of subjects is based, at least in part, or research work conducted by the present inventors. In some embodiments, such research work comprises identifying genes and SNPs robustly associated with the specified disease, one or more of its traits, and/or therapy response. In some embodiments, data for such research may be obtained from scientific data included in articles in peer-reviewed papers and/or available databases for genome-wide analysis studies (GWAS), such as GWAS catalog (www.ebi.ac.uk/gwas), GRASP (grasp.nhlbi.nih.gov/Overview.aspx), etc. In some embodiments, these data include available databases for drug-gene interactions, such as DGIdb (www.dgidb.org/), DrugBank (www.drugbank.ca), etc., and tools such as PRediXcan.

In some embodiments, identified genes may be found to be encoding proteins that are in the same biological pathways of the mechanisms of action of anti-HTN drugs. For example, the ACE gene is known to encode for the ACE protein that is involved in the renin-angiotensin pathway and inhibited by the medication ACE inhibitors to reduce blood pressure.

In some embodiments, this research provides for a database, wherein for each drug, a specific number of genes that are related to response to anti-HTN drugs are assigned.

In some embodiments, a further step may comprise identifying single nucleotide polymorphisms (SNP) that affect significantly the response to an antihypertensive drug. In some embodiments, SNP selection may be based on, e.g.:

Location in genes that are targeted by anti-HTN drugs; and/or statistical significance with respect to HTN, SBP, DBP, and/or PP.

The present inventors have used proprietary and/or publicly available sources to derive genetic association statistics with HTN, SBP, DBP.

In some embodiments, SNPs are selected when they are located in the in promoter or enhancer areas of genes, thus increasing the chances that they affect gene regulation. Promoters and enhancers are two short DNA sequences that serve as the regulatory elements of a gene. Specifically, promoters initiate transcription of a particular gene into proteins that are part of the metabolic pathway where effected by the drugs, and are located near the transcription start of genes. Enhancers can be bound by proteins and they increase the likelihood that transcription of a particular gene will occur. By limiting SNPs selection to those found in gene promoters or enhancers may lead to PSs which better capture the regulation aspects of the gene that are associated with increased with HTN and related traits, and/or linked with a specific antihypertensive drugs, as compared to other variants within the gene.

In some embodiments, with respect to genes satisfying statistical significance criteria, gene regions where promoters and enhancers are located may be identified using publicly available databases, such as GeneHancer. GeneHancer predictions are fully integrated in the widely used GeneCards suite (www.genecards.org) and recently in UCSC genome browser (genome.ucsc.edu). Positions of the gene regions should be aligned with the genome build of the reference genome that the available genetic association data use.

In some embodiments, the present method may further provide for assessing the statistical significance of selected SNPs with respect to HTN, SBP, and DBP, to identify those SNPs representing a statistical significance of, e.g., at least 0.05, between 0.01-0.10, or another specified statistical threshold. Alternatively, SNP selection may include all SNPs from all gene areas and/or representing all statistical significance level. In some embodiments, SNP selection may include only SNPs representing genome-wide significant (i.e., P value <5×10-8) SNPs that are located in the genes of interest. In some embodiments, one or more of these SNP selection strategies may be combined.

For example, table 1 below summarizes exemplary promoter and enhancer regions for the ACE gene that is targeted by ACE Inhibitors.

TABLE 1

Promoter and enhancer regions for ACE gene that is targeted by ACE Inhibitors.

| Drug | Target gene | Chromosome | Position (hg19) | Function |
|---|---|---|---|---|
| ACEI | ACE | 17 | 61554422-61599205 | Gene |
| ACEI | ACE | 17 | 61551058-61556950 | Promoter/Enhancer |
| ACEI | ACE | 17 | 61562201-61562303 | Promoter/Enhancer |
| ACEI | ACE | 17 | 61508611-61515166 | Promoter/Enhancer |
| ACEI | ACE | 17 | 61626418-61630304 | Promoter/Enhancer |
| ACEI | ACE | 17 | 61431510-61431613 | Enhancer |
| ACEI | ACE | 17 | 62090924-62103850 | Promoter/Enhancer |
| ACEI | ACE | 17 | 61497048-61498662 | Enhancer |

TABLE 1-continued

Promoter and enhancer regions for ACE gene that is targeted by ACE Inhibitors.

| Drug | Target gene | Chromosome | Position (hg19) | Function |
|---|---|---|---|---|
| ACEI | ACE | 17 | 61505277-61506104 | Enhancer |
| ACEI | ACE | 17 | 61689560-61689960 | Enhancer |
| ACEI | ACE | 17 | 61594421-61594870 | Enhancer |
| ACEI | ACE | 17 | 61502881-61503030 | Enhancer |
| ACEI | ACE | 17 | 61656647-61657871 | Enhancer |
| ACEI | ACE | 17 | 61500762-61501161 | Enhancer |
| ACEI | ACE | 17 | 60855121-60860435 | Enhancer |
| ACEI | ACE | 17 | 61574731-61577281 | Enhancer |
| ACEI | ACE | 17 | 60972606-60973907 | Enhancer |

With continues reference to step 104 in FIG. 1, in some embodiments, one or more polygenic score (PS) may be calculated with respect to, based on the identified SNPs.

In some embodiments, PSs may be calculated using any suitable algorithm, e.g., any prediction methods that uses genotype data as input. In some embodiments, the selected methodology may be suited for using GWAS summary statistics when genotype data are unavailable. In some embodiments, the selected methodology allows for the inclusion of all available variants in the derived polygenic score, by shrinking effect estimates weights based on an external linkage disequilibrium (LD) reference panel. Taking into account he LD information increases the predictive ability of the polygenic score, compared to other methods that do not account for the effect of LD. In some embodiments, additional and/or alternative methodologies may be used to derive PSs.

In some embodiments, at step 106, a training dataset may be constructed for a machine learning model of the present disclosure.

In some embodiments, a data preprocessing stage may take place, comprising at least one of data cleaning and normalizing, data quality control, and/or any other suitable preprocessing method or technique. Biological data derived from clinical samples may suffer from variations that can arise due to different sample collection or sample preparation procedures, due to quantification inaccuracies, due to batch effects, and/or due to any other technical bias that may lead to mistakes in the analysis. Therefore, in some embodiments, preprocessing may comprise, e.g., quality control, data cleaning, data normalizing; and/or statistical tests based on key statistical measures.

In some embodiments, one or more feature selection, feature extraction, and/or dimensionality reduction steps may be performed with respect to the value sets. In some embodiments, feature selection and/or dimensionality reduction steps may be performed, to reduce the number of variables in each sample pair and/or to obtain a set of principal variables, e.g., those variables that may have significant predictive power. In some embodiments, dimensionality reduction selects principal variables, e.g., proteins, based on the level of response predictive power a variable generates with respect to the desired prediction. In some embodiments, any suitable feature selection and/or dimensionality reduction method or technique may be employed.

In some embodiments, a machine learning model of the present disclosure may be created by training a machine learning algorithm to map genotype and other clinical data to a response to anti-hypertension drugs; diabetes-related drugs; lipid lowering drugs; cardiovascular drugs for IHD, CHF and arrythmias; and/or minimally invasive surgical and/or diagnostic procedures.

In some embodiments, an annotated training dataset of the present disclosure may be used to train the machine learning algorithm, by minimizing a prediction error of the algorithm. In some embodiments, at the end of the training stage, a validation and/or cross-validation stage will be performed by evaluating the trained model on, e.g., a reserved portion of the training dataset.

Accordingly, in some embodiments, a training dataset for a machine learning model of the present disclosure may comprise one or more of genetic data associated with a polygenic score representing predisposition and/or susceptibility in a subject to the cardiovascular or cardiometabolic disease and/or one or more traits associated with the cardiovascular or cardiometabolic disease; and genetic data associated with a polygenic score representing predisposition and/or susceptibility in a subject to respond to one or more treatments or therapies associated with a cardiovascular or cardiometabolic disease.

Accordingly, in some embodiments, an exemplary training dataset of the present disclosure may comprise one or more of:

(i) PSs representing a genetic predisposition in each of a cohort of subjects with respect to respond to one or more therapies from a set of antihypertensive pharmacotherapies; and
(ii) PSs representing a genetic predisposition in each of a cohort of subjects with respect to the cardiovascular or cardiometabolic disease and/or one or more traits associated with the cardiovascular or cardiometabolic disease, e.g., HTN, e.g., blood pressure trait including systolic blood pressure (SBP) and diastolic blood pressure.

Response to drug therapy may be affected by a plurality of reasons. In addition to genetic make-up captured through the PSs corresponding to each anti-HTN medication, other factors such as age, body size, consumption of foods may affect drug response, as well as other treatment taken by the subject and/or other co-morbidities existing in the subject.

Accordingly, in some embodiments, a training dataset of the present disclosure may comprise additional information, such a clinical, demographic, and/or physical information with respect to at least some of the subject in the cohort. For example, in some embodiments, such data may include, but is not limited to:

demographic information (ex, age, ethnicity),
hematological and chemistry measurements,
general medical history, including smoking history and drinking habits, background diseases including hypertension, diabetes, ischemic heart disease, renal insufficiency, chronic obstructive pulmonary disease, asthma, liver insufficiency, Inflammatory Bowel Disease, autoimmune diseases, endocrine diseases, and others,
family medical history, especially of cardiovascular disease and/or cardiometabolic disease,
genetic information, e.g. mutations, gene amplifications, and others (e.g. EGFR, BRAF),
physical parameters, e.g., temperature, pulse, height, weight, BMI, blood pressure, complete blood count, liver function, renal function, electrolytes,
medication (prescribed and non-prescribed),
relative lymphocyte count,
neutrophil to lymphocyte ratio,
baseline protein levels in the plasma (e.g. LDH),
marker staining (e.g. PD-L1 in the tumor or in circulating tumor cells).
Dietary habits,
cholesterol parameters, co-morbidities, e.g., cardiovascular, respiratory, endocrine, digestive, skin, musculoskeletal, mental health, eye/ear, urogenital, neurological blood forming/lymphatics, infectious, non-pulmonary cancer and pulmonary cancer, physical activity parameters, stress parameters, imaging studies, ECG studies, and/or Allergies.

In some embodiments, at least some of the training dataset may be annotated with category labels denoting a response and/or outcome in the respective subject to one or more therapies from a set of antihypertensive pharmacotherapies.

In some embodiments, the annotation may be binary, e.g., positive/negative, responsive/non-responsive, and/or expressed on a scale, e.g., of 1-5 or complete response, partial response, stable disease, or progressive disease. In some embodiments, additional and/or other annotation schemes may be employed.

In some embodiments, one or more annotation schemes may be employed with respect to the training dataset. Accordingly, in some embodiments, a training dataset for a machine learning model of the present disclosure may comprise a plurality of PSs with respect to at least some of the subjects in the cohort, wherein at least some of these PSs may be annotated with category labels denoting a response and/or outcome of the treatment in the respective subject. In some embodiments, such annotation may be binary, e.g., positive/negative, and/or expressed in discrete categories, e.g., on a scale of 1-5. In some embodiments, a binary value category label may be expressed, e.g., as 'yes/no,' 'responsive/non-responsive,' or 'favorable/non-favorable response.' In some embodiments, discrete category labels and/or annotations may be expressed on a scale, e.g., 'complete response,' 'partial response,' 'stable disease,' 'progressive disease,' and 'hyper-progression disease.' In some embodiments, additional and/or other scales and/or thresholds and/or response criteria may be used, e.g., a gradual scale of 1 (non-responsive) to 5 (responsive). In some embodiments, category labels may be associated with adverse or any other secondary effects or response by a subject, e.g., therapy side-effects. For example, in the context of antihypertensive treatment, the response may be indicated as associated with a reduction in HTN, BSP and/or DBP.

In some embodiments, additional and/or other annotation schemes may be employed. In some embodiments, the training dataset may be annotated with, e.g., subject demographic and/or clinical data as detailed above, as further detailed above.

In some embodiments, at step 108, a machine learning model may be trained on the training dataset constructed in step 106. In some embodiments, any suitable machine learning algorithm or combination of methods may be employed, including, but not limited to support vector machine (SVM), penalized logistic regression (PLR), random forest (RF), eXtreme gradient boosting (XGB), ensemble learning, neural networks, etc.

In some embodiments, the machine learning model may be configured to calculate for treatment or treatment combination a success rate and an area-under-receiver-operator curve (AUC). The closer the AUC is to 1, the better is the overall performance of the mode. Values >0.8 can be considered as very good, whereas values >0.7 as fair. In this curve, the x-axis represents the false positive rate and the y-axis shows the true positive rates. The "positive" set comprises subjects who received a specified drug treatment and met the criterion of SBP/DBP lowering in a specific time frame. Negative results may comprise subjects who received the treatment but failed to meet the criterion.

In some embodiments, the model may use propensity score matching to examine whether a specific drug treatment or combination achieves higher success rates, to eliminate as much as possible the effect of subject variability. The model may use, e.g., the following features for the matching: antihypertensive treatment, initial BP, weight, age, BMI, and smoking status, HTN risk overall PS, and drug-specific PS.

In some embodiments, at an inference step 110, a trained machine learning model of the present disclosure may be applied to target data, e.g., a target set PS scores and/or clinical and demographic data as described above, associated with a target subject. In some embodiments, the inference of the trained machine learning model on the target data produces a therapy response prediction.

In some embodiments, at step 112, a therapy course with respect to the target subject may be administered, adjusted, and/or modified based, at least in part, on the inference step 110. In some embodiments, such therapy adjustment may include prescribing a subsequent and/or supplementary therapy for the target subject.

Experimental Results

The present inventors conducted a study to test the prediction power of a machine learning model of the present disclosure.

The study used data associated with pre- and post-HTN treatment measurements in 1,493 patients. The data was obtained from UKBiobank (www.ukbiobank.ac.uk).

The study included patients receiving a single drug treatment and showing a positive reduction in BP. Of the total number of patients, 262 received ACE, 198 received Ca channel blockers, and 50 received Beta Blockers.

Specifically, the study included patients showing BP reduction by more than a mean value (18.11 ACE, 18.42 Ca, 17.44 B Blockers), as well as those showing a reduction in BP to less than 140 mmHg.

PSs were calculated for overall genetic SBP risk, based on analyzing 7,000,000 SNPs. The study captured variations on 7000 SNPs found in the enhancer/promoter zone in drug-related genes that were found to be related to BP.

Drug-specific PSs were calculated for each of the drugs, based on these identified SNPs. The study analyzed systolic and diastolic pressure separately.

A machine learning model was trained on the calculated overall genetic SBP risk and drug-specific PSs, as well as clinical data (including pre-treatment BP, BMI, gender, smoking habits, and alcohol consumption).

The results are summarized in Table 2 below:

| | Systolic difference (mmHg) | P - Value | Diastolic difference (mmHg) | P - value | ML AUC prediction <= 140 | ML AUC prediction Reduction > Mean |
|---|---|---|---|---|---|---|
| ACE I | −5.39 | 0.025 | −2.59 | 0.039 | 0.86 | 0.77 |
| B-Blocker | −6.8 | 0.13 | −0.13 | — | 0.80 | 0.86 |
| Ca channel blockers | −6.57 | 0.012 | −1.7 | 0.11 | 0.78 | 0.83 |

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The description of a numerical range should be considered to have specifically disclosed all the possible subranges as well as individual numerical values within that range. For example, description of a range from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system comprising:
at least one hardware processor; and
a non-transitory computer-readable storage medium having stored thereon program code, the program code executable by the at least one hardware processor to:
obtain, from each of a plurality of subjects, each having a specified type of cardiovascular or cardiometabolic disease a biological sample;
analyze the sample to identify at least one first single nucleotide polymorphism (SNP) associated with a trait of the disease;
calculate a first polygenic score based on the identified at least one first SNP;
select from the identified at least one first SNP one or more second SNP that affects a response to a therapy for treating a cardiovascular or cardiometabolic disease;
calculate a second polygenic score, based on the one or more said second SNP;
at a training stage, train a machine learning model on a training set comprising (a) the first polygenic score and the second polygenic score, and (b) labels associated with a response in each of said subjects to at least one therapy; and
at an inference stage, apply the trained machine learning model to the first polygenic score and the second polygenic score pertaining to a target subject of the plurality of subjects, to predict a response of said target subject to at least one therapy from a set of therapies for treating a cardiovascular or cardiometabolic disease,
wherein selecting the one or more second SNP is based on:
(a) location in genes that affect a target of said therapy, and
(b) statistical significance with respect to said trait of the disease.

2. The system of claim 1, wherein said second score is calculated, based, at least in part, on identifying the second SNP in said target subject.

3. The system of claim 1, wherein said machine learning model is trained on a training set that comprises: (a) said first polygenic score; (b) said second polygenic score; and (c) labels associated with a response in each of said plurality of subjects to said at least one therapy, wherein said labels comprise a positive set, corresponding to first selected subjects who have received a specified drug treatment and met a criterion of response to said therapy, and a negative set, corresponding to second selected subjects who have received the drug treatment but failed to meet the criterion.

4. The system of claim 3, wherein said trait is blood pressure risk, and wherein said first score is a polygenic score calculated, based, at least in part, on identifying said first SNP in said target subject.

5. The system of claim 1, wherein said first score and said second score are calculated in real time, based, on parallel calculation per each chromosome.

6. The system of claim 1, wherein said second SNP is in a gene promoter or in a gene enhancer region.

7. The system of claim 1, wherein said set of therapies is selected from the group consisting of: Ace inhibitors; Angiotensin receptor lockers; Thiazides; Thiazide like; Beta blockers; Alpha antagonists; Alpha blockers; Vasodilators; Aldosterone antagonist; Renal denervation and Barostimulation Biguanides; Sulfonylureas; Meglitinide derivatives; Alpha-glucosidase inhibitors; Thiazolidinediones (TZDs); Glucagonlike peptide-1 (GLP-1) agonists; Dipeptidyl peptidase IV (DPP-4) inhibitors; Selective sodium-glucose transporter-2 (SGLT-2) inhibitors; Insulins; Amylinomimetics; Bile acid sequestrants; Dopamine agonists and bariatric surgery for Type 2 Diabetes; Antilipemic agents; Nicotinic acids; Bile sequestrants; Aspirin, Anti coagulants; Anti platelet; Nitrates; anti-inflammatory agents; DNA methyltransferase inhibitors; antiarrhythmic agents; cardiac and neurological interventions; heart transplants; Digoxin; Ionotropic agents; ivabradine; sacubitril/valsartan; histone deacetylase inhibitors; lifestyle regimens; dietary regimens; and physical activity regimens.

8. The system of claim 1, wherein said trait is selected from a list consisting of: hypertension, systolic blood pressure (SBP), diastolic blood pressure (DBP), high blood glucose levels, diabetes, hypercholesterolemia, high lipids levels, coronary heart disease, heart failure, obesity, arrhythmia, and any combination thereof.

9. The system of claim 1, wherein said response in each of said plurality of subjects and said target subject to said one or more specified therapies comprises at least one of: lowering of SBP, lowering of DBP, lowering of blood glucose levels, lowering of blood lipids levels, improving of coronary heart disease symptoms, improving of heart failure symptoms, lowering weight, and improving of arrhythmia symptoms.

10. The system of claim 1, wherein said training set further comprises, with respect to at least some of said plurality of subjects, labels associated with clinical data selected from the group consisting of: SBP, DBP, age, sex, body mass index (BMI), diet parameters, cholesterol parameters, co-morbidities, physical activity parameters, family history of cardiovascular disease and/or cardiometabolic disease, stress parameters, alcohol consumption parameters, and smoking and tobacco usage, lab results, imaging studies, ECG studies additional medication, response and adverse effect of medications, allergies, RNA profile, single cell RNA sequencing, metabolomics, microbiome, genomics, epigenomics, and MicroRNA.

11. A method comprising:
obtaining a biological sample from each of a plurality of subjects, each having a specified type of cardiovascular or cardiometabolic disease;
analyzing the sample to identify at least one first SNP associated with a trait of the disease;
calculating at least one first polygenic score based on the identified at least one first SNP;
selecting from the identified at least one first SNP one or more second SNP that affects a response to a therapy for treating a cardiovascular or cardiometabolic disease;
calculating a second polygenic score, based on the one or more said second SNP;
at a training stage, training a machine learning model on a training set comprising (a) the first polygenic score and the second polygenic score, and (b) labels associated with a response in each of said subjects to at least one therapy; and
at an inference stage, applying the trained machine learning model to the first polygenic score and the second polygenic score pertaining to a target subject of the plurality of subjects, to predict a response of said target subject to at least one therapy from a set of therapies for treating a cardiovascular or cardiometabolic disease, wherein selecting the one or more second SNP is based on: (a) location in genes that affect a target of said therapy, and (b) statistical significance with respect to said trait of the disease.

12. The method of claim 11, wherein said second score is calculated, based at least in part, on identifying the second SNP in said target subject.

13. The method of claim 11, wherein said machine learning model is trained on a training set that comprises: (a) said first polygenic score; (b) said second polygenic score; and (c) labels associated with a response in each of said subjects to said at least one therapy, wherein said labels comprise a positive set, corresponding to subjects who have received a specified drug treatment and met a criterion of response to said therapy, and a negative set, corresponding to subjects who have received the drug treatment but failed to meet the criterion.

14. The method of claim 11, wherein said trait is blood pressure risk, and wherein said first score is a polygenic score calculated, based, at least in part, on identifying said first SNP in said target subject.

15. The method of claim 11, wherein said first score and said second score are calculated in real time, based at least on parallel calculation per each chromosome.

16. The method of claim 11, wherein said second SNP is in a gene promoter or in a gene enhancer region.

17. The method of claim 11, wherein said set of therapies is selected from the group consisting of: Ace inhibitors; Angiotensin receptor lockers; Thiazides; Thiazide like; Beta blockers; Alpha antagonists; Alpha blockers; Vasodilators; Aldosterone antagonist; Renal denervation and Barostimulation Biguanides; Sulfonylureas; Meglitinide derivatives; Alpha-glucosidase inhibitors; Thiazolidinediones (TZDs); Glucagonlike peptide-1 (GLP-1) agonists; Dipeptidyl peptidase IV (DPP-4) inhibitors; Selective sodium-glucose transporter-2 (SGLT-2) inhibitors; Insulins; Amylinomimetics; Bile acid sequestrants; Dopamine agonists and bariatric surgery for Type 2 Diabetes; Antilipemic agents; Nicotinic acids; Bile sequestrants; Aspirin, Anti coagulants; Anti platelet; Nitrates; anti-inflammatory agents; DNA methyltransferase inhibitors; antiarrhythmic agents; cardiac and neurological interventions; heart transplants; Digoxin; Ionotropic agents; ivabradine; sacubitril/valsartan; histone deacetylase inhibitors; lifestyle regimens; dietary regimens and physical activity regimens.

18. The method of claim 11, wherein said trait is selected from the group consisting: hypertension, systolic blood pressure (SBP), diastolic blood pressure (DBP), high blood glucose levels, diabetes, hypercholesterolemia, high lipids levels, coronary heart disease, heart failure, obesity, arrhythmia, and any combination thereof.

19. The method of claim 11, wherein said training set further comprises, with respect to at least some of said subjects, labels associated with clinical data selected from the group consisting of: SBP, DBP, age, sex, body mass index (BMI), diet parameters, cholesterol parameters, co-morbidities, physical activity parameters, family history of cardiovascular disease and/or cardiometabolic disease, stress parameters, alcohol consumption parameters, and smoking and tobacco usage, lab results, imaging studies, ECG studies additional medication, response and adverse effect of medications, allergies, RNA profile, single cell RNA sequencing, metabolomics, microbiome, genomics, epigenomics, MicroRNA, and any combination thereof.

* * * * *